(12) United States Patent
Nakao

(10) Patent No.: US 9,096,511 B2
(45) Date of Patent: Aug. 4, 2015

(54) METHOD FOR PRODUCING 2-BROMO-4,5-DIALKOXY BENZOIC ACID

(75) Inventor: Ryu Nakao, Chuo-ku (JP)

(73) Assignee: ZERIA PHARMACEUTICAL CO., LTD., Tokyo (JP)

( * ) Notice: Subject to any disclaimer, the term of this patent is extended or adjusted under 35 U.S.C. 154(b) by 36 days.

(21) Appl. No.: 13/991,242

(22) PCT Filed: Dec. 6, 2011

(86) PCT No.: PCT/JP2011/078169
§ 371 (c)(1),
(2), (4) Date: Jun. 3, 2013

(87) PCT Pub. No.: WO2012/077673
PCT Pub. Date: Jun. 14, 2012

(65) Prior Publication Data
US 2013/0253222 A1 Sep. 26, 2013

(30) Foreign Application Priority Data
Dec. 7, 2010 (JP) .................................. 2010-272668

(51) Int. Cl.
*C07C 65/00* (2006.01)
*C07C 51/363* (2006.01)
*C07C 51/367* (2006.01)

(52) U.S. Cl.
CPC ............. *C07C 51/363* (2013.01); *C07C 51/367* (2013.01)

(58) Field of Classification Search
CPC .................................. C07C 65/21; C07C 65/40
See application file for complete search history.

(56) References Cited

U.S. PATENT DOCUMENTS

| | | |
|---|---|---|
| 7,335,791 B1 | 2/2008 | Ritter et al. |
| 2008/0021221 A1 | 1/2008 | Nagasawa et al. |
| 2008/0139843 A1 | 6/2008 | Ritter |
| 2009/0099175 A1 | 4/2009 | Arrington et al. |

FOREIGN PATENT DOCUMENTS

| | | |
|---|---|---|
| JP | 8 27059 | 1/1996 |
| JP | 2003 252826 | 9/2003 |
| JP | 2009 528374 | 8/2009 |
| JP | 2010 511043 | 4/2010 |
| WO | 2006 022252 | 3/2006 |

OTHER PUBLICATIONS

English Translation of Mais et al. (EP 0691323, 1996).*
International Search Report Issued Mar. 13, 2012 in PCT/JP11/078169 filed Dec. 6, 2011.

* cited by examiner

*Primary Examiner* — Sudhakar Katakam
*Assistant Examiner* — Jennifer C Sawyer
(74) *Attorney, Agent, or Firm* — Oblon, McClelland, Maier & Neustadt, L.L.P.

(57) ABSTRACT

Provided is a method for effectively producing a 4,5-dialkoxy-2-hydroxybenzoic acid from an inexpensive raw material.

A method for producing a 2-bromo-4,5-dialkoxybenzoic acid represented by the following formula (2): (wherein each of $R^1$ and $R^2$ represents a lower alkyl group), the method including causing a 3,4-dialkoxybenzoic acid represented by the following formula (1): (wherein $R^1$ and $R^2$ have the same meanings as defined above) to react with bromine in concentrated hydrochloric acid.

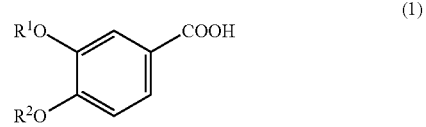

(1)

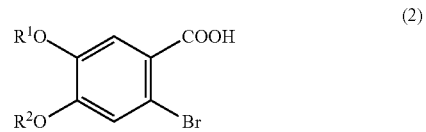

(2)

17 Claims, No Drawings

METHOD FOR PRODUCING 2-BROMO-4,5-DIALKOXY BENZOIC ACID

TECHNICAL FIELD

The present invention relates to a method for producing a 2-bromo-4,5-dialkoxybenzoic acid which is useful as a synthesis intermediate for pharmaceuticals, etc.

BACKGROUND ART 4,5-Dialkoxy-2-hydroxybenzoic acid (3) is known as a raw material or synthesis intermediate of various pharmaceuticals and agricultural chemicals. In a known method for producing 4,5-dialkoxy-2-hydroxybenzoic acid (3), as shown in the following reaction scheme:

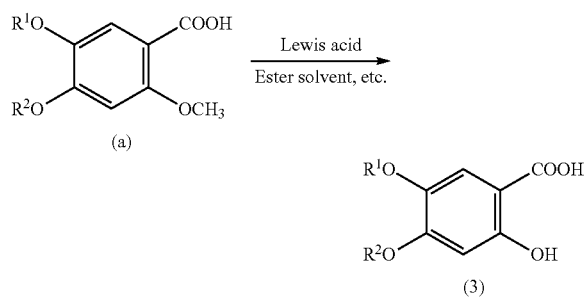

(wherein each of $R^1$ and $R^2$ represents a lower alkyl group), the methoxy group at the 2-position of 2,4,5-trialkoxybenzoic acid (a) is selectively demethylated by causing the acid to react with a Lewis acid in an ester, ketone, or amide solvent (Patent Document 1).

PRIOR ART DOCUMENT

Patent Document

Patent Document 1: WO2006/022252
Patent Document 2: JP-A-2003-252826

SUMMARY OF THE INVENTION

Problems to be Solved by the Invention

However, the aforementioned method involves a problem in that production of 2,4,5-trialkoxybenzoic acid, serving as a raw material, requires an intricate process, resulting in cost increase. In addition, the method requires employment of a metal-containing reagent (e.g., titanium tetrachloride or aluminum chloride) in a stoichiometric amount or more. Since such a metal-containing reagent exhibits low resistance to water, the method must be carried out in a non-aqueous system; i.e., the method requires careful control of the reaction system. The method also involves a problem in that an organic solvent must be used in a large amount.

In view of the foregoing, an object of the present invention is to provide a method for effectively producing a 4,5-dialkoxy-2-hydroxybenzoic acid from an inexpensive raw material.

Means for Solving the Problems

In order to achieve the aforementioned object, the present inventor has focused on a 3,4-dialkoxybenzoic acid serving as an inexpensive raw material, and has conducted studies on means for selectively introducing a hydroxyl group to the 6-position of the compound. Specifically, the present inventor has conducted studies on a method including halogenation of the 6-position of a 3,4-dialkoxybenzoic acid serving as an inexpensive raw material, and hydrolysis of the halogenated compound. In a known method, halogenation reaction of the 6-position of a 3,4-dialkoxybenzoic acid is carried out in an organic solvent such as a halogenated hydrocarbon, an ether, a carboxylic acid, or an ester (Patent Document 2). However, in the case of this method, halogenation also proceeds at a position other than the 6-position of the benzoic acid, and the resultant by-products are difficult to remove, resulting in an unsatisfactory yield (about 78%). Thus, the present inventor has conducted further studies, and as a result has found that, quite unexpectedly, when this halogenation reaction is carried out by use of bromine in concentrated hydrochloric acid, highly selective bromination is achieved at the 6-position of a 3,4-dialkoxybenzoic acid at high yield. The present inventor has also found that when the resultant 2-bromo-4,5-dialkoxybenzoic acid is hydrolyzed in the presence of a copper compound and an amine compound, a high-purity 4,5-dialkoxy-2-hydroxybenzoic acid is produced at high yield. The present invention has been accomplished on the basis of these findings.

Accordingly, the present invention provides a method for producing a 2-bromo-4,5-dialkoxybenzoic acid represented by the following formula (2):

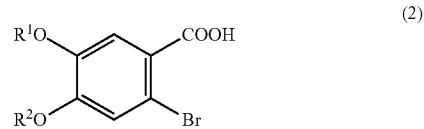

(wherein each of $R^1$ and $R^2$ represents a lower alkyl group), the method comprising causing a 3,4-dialkoxybenzoic acid represented by the following formula (1):

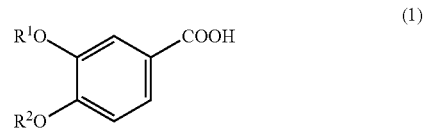

(wherein $R^1$ and $R^2$ have the same meanings as defined above) to react with bromine in concentrated hydrochloric acid.

The present invention also provides a method for producing a 4,5-dialkoxy-2-hydroxybenzoic acid represented by the following formula (3):

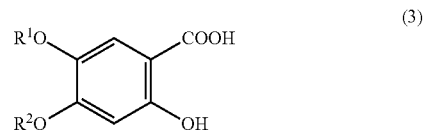

(wherein $R^1$ and $R^2$ have the same meanings as defined above), the method comprising causing a 3,4-dialkoxybenzoic acid represented by the following formula (1):

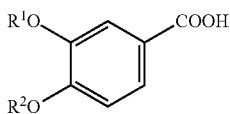

(wherein $R^1$ and $R^2$ have the same meanings as defined above) to react with bromine in concentrated hydrochloric acid; and hydrolyzing the resultant 2-bromo-4,5-dialkoxybenzoic acid represented by the following formula (2):

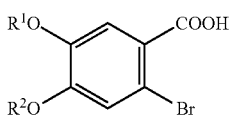

(wherein $R^1$ and $R^2$ have the same meanings as defined above) in the presence of a copper compound and an amine compound.

Effects of the Invention

According to the method of the present invention, high-purity 2-bromo-4,5-dimethoxybenzoic acid is produced, under industrially advantageous reaction conditions, from 3,4-dimethoxybenzoic acid, which is an inexpensive raw material, at high yield, and also high-purity 4,5-dimethoxy-2-hydroxybenzoic acid is produced in an industrially advantageous manner.

MODES FOR CARRYING OUT THE INVENTION

The method of the present invention is represented by the following reaction scheme:

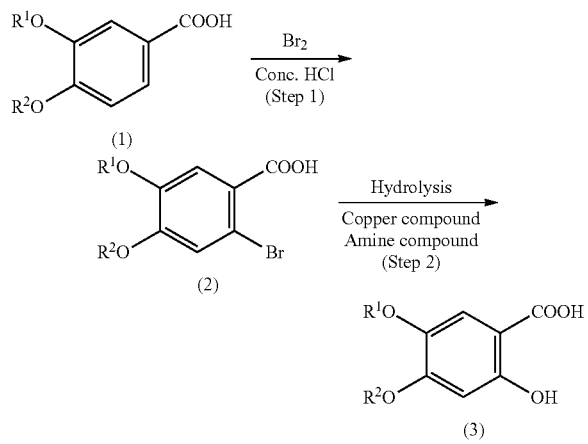

(wherein $R^1$ and $R^2$ have the same meanings as defined above).

[Step 1]

In step 1, a 3,4-dialkoxybenzoic acid represented by formula (1) (hereinafter the acid may be referred to as "compound (1)") is caused to react with bromine in concentrated hydrochloric acid, to thereby produce a 2-bromo-4,5-dialkoxybenzoic acid represented by formula (2) (hereinafter the acid may be referred to as "compound (2)").

In formulas (1) to (3), each of $R^1$ and $R^2$ represents a lower alkyl group. Examples of the lower alkyl group include C1 to C6 linear or branched alkyl groups. Specific examples of the lower alkyl group include methyl, ethyl, n-propyl, isopropyl, and n-butyl. Particularly preferably, both $R^1$ and $R^2$ are a methyl group.

Compound (1), serving as a raw material, is readily available. Particularly, 3,4-dimethoxybenzoic acid, in which both $R^1$ and $R^2$ are a methyl group, is available at low cost.

In the present invention, the reaction corresponding to step 1 is carried out in concentrated hydrochloric acid. Currently, this reaction is carried out in an organic solvent such as ethyl acetate (see Patent Document 2), and it has not been known that the reaction is carried out in an inorganic solvent such as concentrated hydrochloric acid. The hydrogen chloride content of the concentrated hydrochloric acid employed is preferably 30% or more, more preferably 33% or more, even more preferably 33 to 40%.

The amount of bromine employed is preferably 1.0 to 2.0 equivalents, more preferably 1.0 to 1.5 equivalents, particularly preferably 1.0 to 1.1 equivalents, with respect to compound (1). This reaction sufficiently proceeds even when the amount of bromine employed is as small as 1.0 to 1.1 equivalents, and produces small amounts of by-products.

The reaction temperature is preferably 10 to 45° C., particularly preferably 10 to 35° C. The aforementioned reaction proceeds at such a temperature (i.e., ambient temperature) without requiring application of any energy. The reaction time, which may vary with reaction scale, etc., is 2 to 10 hours or 4 to 8 hours. When the reaction time falls within such a range, satisfactory results are obtained.

The aforementioned reaction selectively produces a high-purity 2-bromo-4,5-dialkoxybenzoic acid. According to this reaction, bromination of the 6-position proceeds in a highly selective manner. Therefore, small amounts of by-products are produced, and a high-purity product of interest is produced at high yield.

[Step 2]

In step 2, compound (2) is hydrolyzed in the presence of a copper compound and an amine compound, to thereby produce a 4,5-dialkoxy-2-hydroxybenzoic acid represented by formula (3) (hereinafter the acid may be referred to as "compound (3)").

Examples of the copper compound employed include copper sulfate, cuprous chloride, cupric chloride, cuprous bromide, cupric bromide, cuprous oxide, cupric oxide, copper acetate, and copper powder. Of these, copper sulfate is particularly preferred. Examples of the amine compound include secondary amines, tertiary amines, and aromatic amines. Specific examples of the amine compound include pyridine, dialkylamine, morpholine, piperidine, pyrrolidine, piperazine, and trialkylamine. Of these amine compounds, pyridine is particularly preferred.

The amount of the copper compound employed is preferably 0.01 to 1.0 equivalent, particularly preferably 0.05 to 0.1 equivalents, with respect to compound (2). The amount of the amine compound employed is preferably 0.1 to 5.0 equivalents, particularly preferably 0.5 to 1 equivalent, with respect to compound (2).

The hydrolysis reaction is preferably carried out in the presence of an alkali. Examples of the alkali employed include sodium carbonate, potassium carbonate, sodium hydrogencarbonate, potassium hydrogencarbonate, sodium hydroxide, and potassium hydroxide. The amount by mole of the alkali employed is preferably 1.0 to 3.0 times, particularly preferably 1.25 to 1.5 times, that of compound (2).

The hydrolysis reaction is carried out in an aqueous solution at preferably 50 to 100° C., particularly preferably at 90 to 100° C. The reaction time is preferably 1 to 8 hours, particularly preferably 1 to 3 hours.

After completion of the reaction, a product of interest can be purified through a common technique such as washing, recrystallization, or any chromatography technique.

According to the method of the present invention, a high-purity 4,5-dialkoxy-2-hydroxybenzoic acid (compound (3)) is produced from an inexpensive raw material through a simple process at high yield. Through, for example, the method described in WO2006/022252, compound (3) can be formed into compound (8), which is useful as a drug such as an enterokinesis-improving agent.

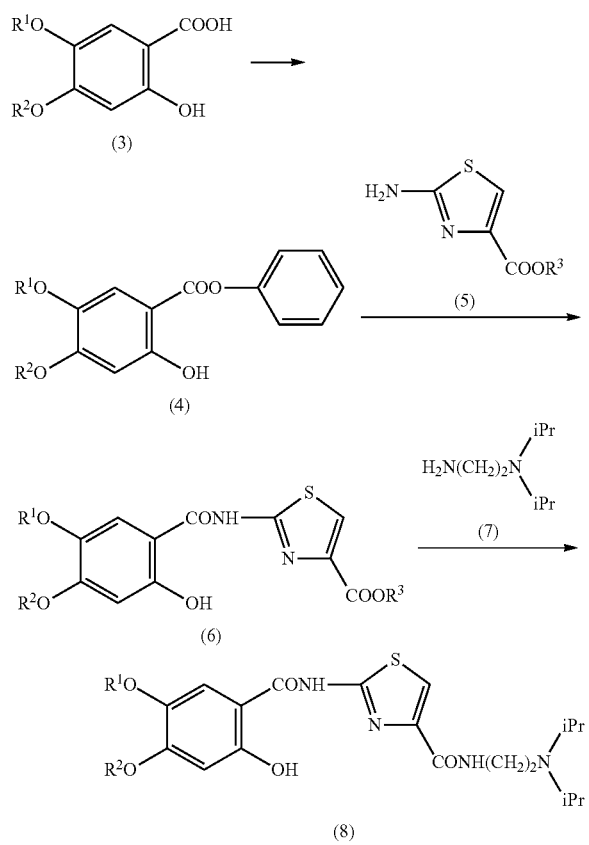

(In the aforementioned scheme, $R^3$ represents a lower alkyl group, and $R^1$ and $R^2$ have the same meanings as defined above.)

Specifically, compound (3) is caused to react with phenol or triphenyl phosphite, to thereby produce compound (4); compound (4) is caused to react with compound (5), to thereby produce compound (6); and compound (6) is caused to react with compound (7), to thereby produce compound (8) or a salt thereof. In this case, $R^3$ is preferably a C1 to C6 alkyl group.

EXAMPLES

The present invention will next be described in more detail by way of examples, which should not be construed as limiting the invention thereto.

Example 1

(Compound (1)→Compound (2))

3,4-Dimethoxybenzoic acid (25.0 g) was suspended in concentrated hydrochloric acid (35%) (500 mL), and bromine (23.0 g, 1.05 equivalents) was added dropwise to the resultant suspension at 25° C. Subsequently, the resultant mixture was stirred for seven hours. Water (500 mL) was added to the mixture, and the mixture was stirred for one hour. Thereafter, the precipitated crystals were filtrated, and then dried under reduced pressure, to thereby produce crude crystals of 2-bromo-4,5-dimethoxybenzoic acid (34.47 g) (yield: 96.2%).

$^1$H-NMR (DMSO-$d_6$, δ): 3.79 (s, 3H), 3.84 (s, 3H), 7.21 (s, 1H), 7.37 (s, 1H), 13.08 (bs, 1H).

The same reaction as described above was carried out under different reaction conditions (i.e., the amount of bromine, the reaction temperature, and the reaction time were varied). Table 1 shows the relationship between reaction conditions and yield. In Table 1, "A" represents 3-bromo-4,5-dimethoxybenzoic acid; "B" 3,4-dimethoxybenzoic acid; "C" 1,2-dibromo-4,5-dimethoxybenzene; "E" 2,3-dibromo-4,5-dimethoxybenzoic acid; and "F" 2,6-dibromo-4,5-dimethoxybenzoic acid.

TABLE 1

| (eq) Amount of bromine | Temperature | (hr) Time | (%) A | B | C | Compound (2) Yield (%) | E | F |
|---|---|---|---|---|---|---|---|---|
| 2.0 | Room temperature | 3 | 1.8 | 0.6 | 1.3 | 85.5 | 4.3 | 6.5 |
| 1.1 | Room temperature | 7 | 1.8 | 1.4 | 3.2 | 90.3 | 2.0 | 1.3 |
| 1.05 | Room temperature | 7 | 0.8 | 1.0 | 1.9 | 92.5 | 2.3 | 1.4 |
| 1.05 | 20 to 30° C. | 5 | — | 1.4 | — | 92.1 | — | — |
| 1.05 | 40 to 45° C. | 5 | — | 4.6 | — | 82.6 | — | — |

As is clear from Table 1, when compound (1) is caused to react with bromine in concentrated hydrochloric acid, high-purity compound (2) is produced at high yield under mild reaction conditions. As is also clear from Table 1, when the amount of bromine employed is 1.0 to 1.1 equivalents, satisfactory results are obtained.

According to the Example of Patent Document 2, bromine (1.8 equivalents) is added to compound (1) in ethyl acetate, and reaction is allowed to proceed at 65° C. for seven hours, to thereby produce compound (2) at a yield of 78%. These data indicate that the method of the present invention is more industrially advantageous than the method described in Patent Document 2.

For evaluation of the effect of concentrated hydrochloric acid concentration, the aforementioned reaction was carried out under the following conditions (amount of bromine: 1.1 equivalents, reaction temperature: 20 to 30° C., and reaction time: three hours), while the concentration of concentrated hydrochloric acid employed was varied. The results are shown in Table 2.

TABLE 2

| | Concentrated hydrochloric acid concentration (Yield %) | | | | | |
|---|---|---|---|---|---|---|
| Product | 30% | 31% | 32% | 33% | 34% | 35% |
| A | 1.13 | 1.24 | 1.37 | 1.25 | 1.09 | 1.05 |
| B | 8.65 | 4.6 | 4.17 | 4.04 | 2.16 | 0.47 |
| C | 10.83 | 6.12 | 4.4 | 3.13 | 2.79 | 1.84 |
| Compound (2) | 75.55 | 82.37 | 85.39 | 89.14 | 91.11 | 95.64 |
| E | 1.77 | 2.47 | 1.78 | 1.16 | 1.19 | 0.75 |
| F | 2.07 | 3.22 | 2.89 | 1.28 | 1.66 | 0.25 |

As is clear from Table 2, the higher the concentrated hydrochloric acid concentration, the higher the yield of compound (2). Even in the case where 30% concentrated hydrochloric acid is employed, when the reaction time is prolonged, the yield of compound (2) is further increased. These data indicate that the concentrated hydrochloric acid concentration is preferably 33% or more.

Example 2

(Compound (2)→Compound (3))

Water (80 mL) was added to the crude crystals of 2-bromo-4,5-dimethoxybenzoic acid produced in Example 1 (20.0 g) and sodium carbonate (10.1 g). The resultant mixture was stirred under heating at 80° C., and a copper sulfate solution prepared from copper sulfate pentahydrate (1.91 g), water (20 mL), and pyridine (3.1 mL) was added to the mixture. The resultant mixture was further heated and stirred at 90 to 100° C. for one hour. The mixture was cooled to 50° C., and concentrated hydrochloric acid (16.0 g) was added dropwise thereto. After cooling of the mixture, the precipitated crystals were filtrated, and then dried under reduced pressure, to thereby produce crude crystals of 2-hydroxy-4,5-dimethoxybenzoic acid (15.08 g) (yield: 99.3%).

$^1$H-NMR (DMSO-d$_6$, δ): 3.71 (s, 3H), 3.81 (s, 3H), 6.56 (s, 1H), 7.17 (s, 1H), 11.22 (bs, 1H), 13.58 (bs, 1H).

The reaction of Example 2 was repeated, except that copper sulfate was replaced with the same equivalent of a copper compound. The same reaction conditions as described above were employed, except that the amount of pyridine employed was changed to 5 equivalents. Table 3 shows the results in terms of yield of compound (3).

TABLE 3

| Copper catalyst | Yield of compound (3) |
|---|---|
| Copper sulfate | 96.80% |
| Copper powder | 92.20% |
| Cuprous bromide | 98.80% |
| Cupric bromide | 93.40% |
| Cuprous chloride | 98.30% |
| Cuprous oxide | 97.20% |
| Cupric oxide | 98.60% |
| Copper acetate | 97.10% |

When the reaction of Example 2 was repeated, except that the amount of pyridine employed was changed to 0.1 equivalents (0.62 mL), compound (3) was produced at a yield of 83.4% (reaction time: eight hours). When the reaction of Example 2 was repeated, except that the amount of pyridine employed was changed to 1.0 equivalent (6.2 mL), compound (3) was produced at a yield of 91.5% (reaction time: three hours).

Referential Example (1) Toluene (1.5 g) was mixed with P(OPh)$_3$ (2.35 g), 2-hydroxy-4,5-dimethoxybenzoic acid (1.5 g), and H$_2$SO$_4$ (40.3 µL) under a stream of argon, and the resultant reaction mixture was refluxed with stirring for 2.5 hours. The reaction mixture was cooled, and methanol (5 g) was added, followed by stirring for 30 minutes. Subsequently, water (2.5 g) was added to the mixture, and the mixture was stirred for 30 minutes. The precipitated crystals were filtrated, and then dried under reduced pressure, to thereby produce phenyl 2-hydroxy-4,5-dimethoxybenzoate (2.0 g) at a yield of 96%.

(2) Phenyl 2-hydroxy-4,5-dimethoxybenzoate (5.0 g), methyl 2-amino-1,3-thiazole-4-carboxylate (3.75 g), and (PhO)$_3$B (5.49 g) were suspended in toluene (25 g) under a stream of argon, and the resultant suspension was stirred under heating at 100° C. for three hours. Methanol (25 g) was added dropwise to the reaction mixture at 70° C., and then the resultant mixture was refluxed for one hour. The mixture was cooled, and stirred at 30° C. or lower for one hour. Thereafter, the precipitated crystals were filtrated, and then dried at 60° C. under reduced pressure, to thereby produce 2-[(2-hydroxy-4,5-dimethoxybenzoyl)amino]-1,3-thiazole-4-carboxylic acid methyl ester monomethanol solvate (6.49 g) at a yield of 96%. The 2-[(2-hydroxy-4,5-dimethoxybenzoyl)amino]-1,3-thiazole-4-carboxylic acid methyl ester monomethanol solvate was found to have a purity of 99.78% as determined through HPLC (i.e., very high purity).

$^1$H-NMR (DMSO-d$_6$, δ): 3.19 (s, 3H), 3.79 (s, 3H), 3.83 (s, 3H), 3.84 (s, 3H), 4.05-4.15 (bs, 1H), 6.61 (s, 1H), 7.63 (s, 1H), 8.13 (s, 1H), 11.77 (s, 1H), 12.40 (s, 1H).

Furthermore, drying was carried out at 100° C. under reduced pressure, to thereby produce 2-[(2-hydroxy-4,5-dimethoxybenzoyl)amino]-1,3-thiazole-4-carboxylic acid methyl ester.

$^1$H-NMR (DMSO-d$_6$, δ): 3.79 (s, 3H), 3.83 (s, 3H), 3.84 (s, 3H), 6.61 (s, 1H), 7.63 (s, 1H), 8.13 (s, 1H), 11.77 (s, 1H), 12.40 (s, 1H).

(3) The 2-[(2-hydroxy-4,5-dimethoxybenzoyl)amino]-1,3-thiazole-4-carboxylic acid methyl ester (10.81 g) was suspended in toluene (30 mL), and diisopropylethylenediamine was added dropwise at 70° C. under a stream of argon. Thereafter, the resultant mixture was stirred under heating at 100° C. for five hours. The resultant reaction mixture was cooled, and 10% (w/w) aqueous sodium chloride solution (20 mL) was added to the mixture at 75° C., followed by extraction operation. This operation was carried out once again. After removal of the resultant aqueous layer, toluene was distilled off under reduced pressure, and the residue was diluted with 80% (v/v) 2-propanol-water (38 mL). 35% Hydrochloric acid (9.22 g) was added dropwise to the diluted residue, to thereby precipitate N-[2-(diisopropylamino)ethyl]-2-[(2-hydroxy-4,5-dimethoxybenzoyl)amino]-1,3-thiazole-4-carboxamide hydrochloride. The precipitated crystals were filtrated and washed with 2-propanol, and then dried at 50° C. under reduced pressure, to thereby produce N-[2-(diisopropylamino)ethyl]-2-[(2-hydroxy-4,5-dimethoxybenzoyl)amino]-1,3-thiazole-4-carboxamide hydrochloride (14.45 g) at a yield of 97%.

$^1$H-NMR (DMSO-d$_6$, δ): 1.32 (d, 6H, J=6.4 Hz), 1.35 (d, 6H, J=6.4 Hz), 3.16-3.19 (m, 2H), 3.59-3.67 (m, 4H), 3.78 (s, 3H), 3.82 (s, 3H), 6.89 (s, 1H), 7.50 (s, 1H), 7.91 (s, 1H), 8.74 (t, 1H, J=5.9 Hz), 9.70 (s, 1H), 11.80 (s, 1H), 12.05-12.15 (bs, 1H).

The invention claimed is:

1. A method for producing a 2-bromo-4,5-dialkoxybenzoic acid, the method comprising:

reacting a 3,4-dialkoxybenzoic acid with bromine in concentrated hydrochloric acid, thereby obtaining the 2-bromo-4,5-dialkoxybenzoic acid wherein said reacting is at a temperature ranging from 10 to 35° C., wherein the 2-bromo-4,5-dialkoxybenzoic acid is of formula (2):

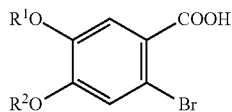

(2)

each of $R^1$ and $R^2$ is a lower alkyl group, and
the 3,4-dialkoxybenzoic acid is of formula (1):

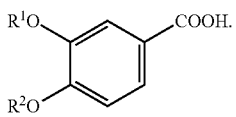

(1)

2. The method according to claim 1, wherein the concentrated hydrochloric acid has a hydrogen chloride content of 33% or more.

3. The method according to claim 1, wherein an amount of bromine in the reacting is from 1.0 to 1.1 equivalents.

4. The method according to claim 1, wherein a temperature of the reacting is achieved without application of energy.

5. The method according to claim 1, wherein both $R^1$ and $R^2$ are methyl.

6. A method for producing a 4,5-dialkoxy-2-hydroxybenzoic acid, the method comprising:
reacting a 3,4-dialkoxybenzoic acid with bromine in concentrated hydrochloric acid, thereby obtaining a 2-bromo-4,5-dialkoxybenzoic acid wherein said reacting is at a temperature ranging from 10 to 35° C., and
hydrolyzing the 2-bromo-4,5-dialkoxybenzoic acid in the presence of a copper compound and an amine compound, thereby obtaining the 4,5-dialkoxy-2-hydroxybenzoic acid,
wherein the 4,5-dialkoxy-2-hydroxybenzoic acid is of formula (3):

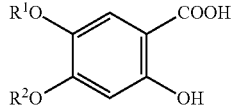

(3)

each of $R^1$ and $R^2$ is a lower alkyl group, the 3,4-dialkoxybenzoic acid is of formula (1):

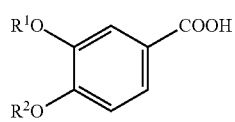

(1)

and the 2-bromo-4,5-dialkoxybenzoic acid is of formula (2):

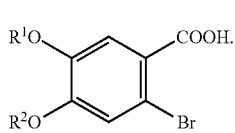

(2)

7. The method according to claim 6, wherein the copper compound is selected from the group consisting of copper sulfate, cuprous chloride, cupric chloride, cuprous bromide, cupric bromide, cuprous oxide, cupric oxide, copper acetate, and copper powder.

8. The method according to claim 6, wherein the amine compound is selected from the group consisting of pyridine, dialkylamine, morpholine, piperidine, pyrrolidine, piperazine, and trialkylamine.

9. The method according to claim 6, wherein the hydrolyzing is under an alkaline condition.

10. The method according to claim 6, wherein the concentrated hydrochloric acid has a hydrogen chloride content of 30% or more.

11. The method according to claim 6, wherein an amount of bromine in the reacting is from 1.0 to 1.1 equivalents.

12. The method according to claim 6, wherein reacting the 3,4-dialkoxybenzoic acid with bromine is achieved without application of energy.

13. The method according to claim 6, wherein both $R^1$ and $R^2$ are methyl.

14. The method according to claim 1, wherein the concentrated hydrochloric acid has a hydrogen chloride content of 33% to 40%.

15. The method according to claim 1, wherein an amount of bromine in the reacting is from 1.0 to 1.5 equivalents.

16. The method according to claim 6, wherein the concentrated hydrochloric acid has a hydrogen chloride content of 33% to 40%.

17. The method according to claim 6, wherein an amount of bromine in the reacting is from 1.0 to 1.5 equivalents.

* * * * *